Feb. 4, 1964 C. FISCHER Plant Pat. 2,356
GLADIOLUS PLANT
Filed Oct. 16, 1962
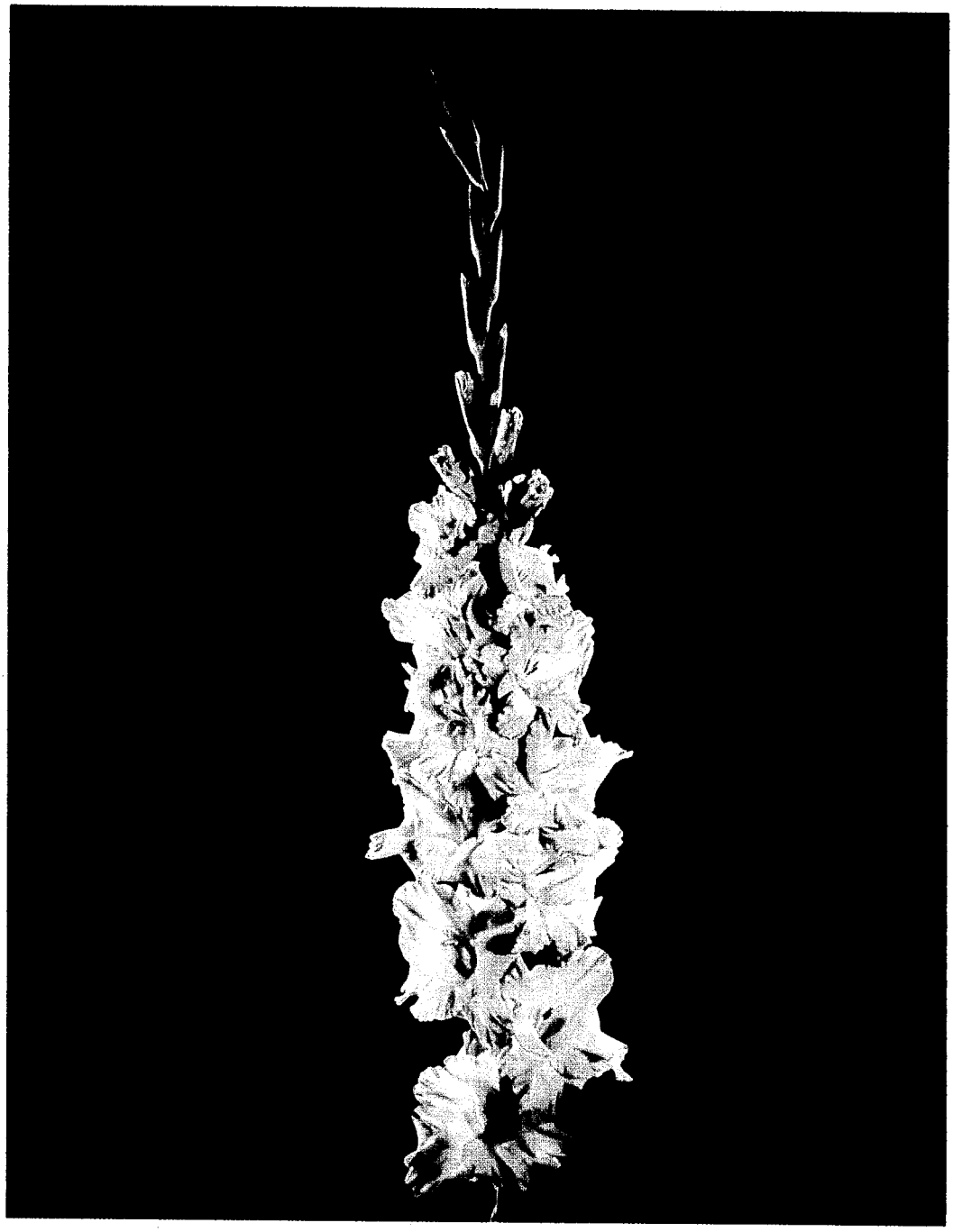
Inventor.
Carl Fischer
By: Robb & Robb
Attorneys.

United States Patent Office

Plant Pat. 2,356
Patented Feb. 4, 1964

2,356
GLADIOLUS PLANT

Carl Fischer, St. Charles, Minn., assignor to Imperial Flowers Limited, Leamington, Ontario, Canada, a corporation of Canada Filed Oct. 16, 1962, Ser. No. 231,050
1 Claim. (Cl. Plt.—85)

The present invention relates to a new and distinct variety of gladiolus plant which was originated by me by crossing the variety known as "Campanile" (unpatented) with the variety known as "Innocence" (unpatented), the former being the seed parent, and the latter being the pollen parent, said cross having been made by me by manual cross-pollination in my breeding fields at St. Charles, Minnesota.

The primary objective of this breeding was to produce a new gladiolus variety having flowers of a more beautiful lavender shade. This objective was fully achieved, along with other desirable improvements, as evidenced by the following characteristics which are outstanding in the new variety and which distinguish it from its parents, as well as from all other varieties of which I am aware:

(1) The habit of fresh flower opening in good number at one time;

(2) Intense ruffling and needle-pointing of the flower petals;

(3) Heavy petal substance; and (4) Extreme beauty of the flowers as evidenced by the good length of the flowerheads, clean styling thereof, and a distinctive and attractive general color tonality corresponding to Mallow Purple, with creamy white blotch and midribs.

My new variety resembles the variety known as "Lohengrin" (unpatented) more than any other, but differs principally therefrom by having shorter flower stems, a habit of opening much better from tight buds, longer flowerheads, more heavily ruffled flowers, heavier petal substance, a more pleasing flower form, and a more attractive flower appearance, including a more attractive throat blotch.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely vigorous; prolific propagator; average height ranges from 54 inches to 58 inches.

Blooming habit: Mid-season bloomer in the Northern latitudes of the United States; comes into bloom from large bulbs in about 80 days; bears from 22 to 24 buds per spike, with from 10 to 12 florets opening at one time, and 6 or 7 buds showing color.

Stems: Stiff; straight.

*Diameter at base.*—From about ½ inch to ⅝ inch.

*Color (just above bulb).*—Mallow Purple, Plate 630/1.

Foliage: Upright; leaves average about 36 inches tall and about 1¾ inches wide. Color—healthy green.

Disease resistance: Very good resistance to Septoria leaf spot and Fusarium yellows, but only average resistance to Sclerotina dry rot, as determined by comparison with other varieties grown in my fields near St. Charles, Minnesota, in irrigated black loam soil.

Corms (bulbs): Healthy; average diameter about 2 inches; husks give rough appearance. Color of flesh—Maize Yellow, Plate 607/2.

*Flower*

Spike: Tall; flowerhead ranges from about 24 inches to 30 inches long; averages from 22 to 24 buds, with from 10 to 12 fresh florets open at once and 6 or 7 buds showing color.

Bud:

*Size.*—From 3 inches to 3½ inches long when opening.

*Opening.*—Opens well; 6 or 7 buds show color at one time.

Flower:

*Arrangement.*—Florets are formally arranged in a double row on the stems, but do not always face forward.

*Size.*—Lower florets average from 5 inches to 5¼ inches in diameter, with upper florets being progressively smaller.

*Form.*—Florets are round, extremely heavily ruffled and creased, and are somewhat needle-pointed.

*Keeping qualities.*—Keeps well.

Petals:

*Shape.*—Round; intensely ruffled; recurved; needle-pointed.

*Size.*—Outer petals—about 2½ inches wide. Inner petals—about 2¼ inches wide.

*Aspect.*—Extremely heavy substance; smooth surface; often creased along the midrib.

*Fragrance.*—None.

*Color.*—General color effect is between Mallow Purple, Plate 630/2 and Mallow Purple, Plate 630/1, with inside of floret shading lighter to Mallow Purple, Plate 630/3, and with creamy white blotch and midribs; streaks of Mallow Purple, Plate 630/1 occur on reverse of petals and extend from base outward where petals meet at calyx.

*Reproductive Organs*

Stamens: Color—Veronica Violet, Plate 639.

Pistil: Color—white.

I claim:

A new and distinct variety of gladiolus plant, substantially as herein shown and described, characterized particularly as to novelty by the unique combination of a habit of flower opening in goodly number at one time, and intense ruffling and needle-pointing of the flower petals, heavy flower petal substance, and a distinctive and attractive Mallow Purple general color tonality of the flowers, said flowers having creamy white blotches and midribs, clean styling and good length of heads.

No references cited.